United States Patent
Serex (10) Patent No.: US 12,151,243 B2
(45) Date of Patent: Nov. 26, 2024

(54) MICRO-FLUIDIC PARTICLE CONCENTRATOR AND FILTERING DEVICE

(71) Applicant: ECOLE POLYTECHNIQUE FEDERALE DE LAUSANNE (EPFL), Lausanne (CH)

(72) Inventor: Ludovic Serex, Pully (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 225 days.

(21) Appl. No.: 17/373,811

(22) Filed: Jul. 13, 2021

(65) Prior Publication Data

US 2021/0395659 A1 Dec. 23, 2021

Related U.S. Application Data

(62) Division of application No. 16/052,793, filed on Aug. 2, 2018, now abandoned.

(30) Foreign Application Priority Data

Aug. 4, 2017 (EP) .................................... 17184837

(51) Int. Cl.
*B01L 3/00* (2006.01)
*B33Y 10/00* (2015.01)
(Continued)

(52) U.S. Cl.
CPC ... *B01L 3/502753* (2013.01); *B01L 3/502707* (2013.01); *B01L 3/502761* (2013.01); *B33Y 10/00* (2014.12); *C12M 21/08* (2013.01); *C12M 29/04* (2013.01); *C12M 29/06* (2013.01); *C12M 47/02* (2013.01); *G01N 1/4077* (2013.01);
(Continued)

(58) Field of Classification Search
CPC ....... B01L 2200/027; B01L 2200/0647; B01L 2200/0652; B01L 2300/0681; B01L 2400/049; B01L 3/502707; B01L 3/502753; B01L 3/502761; C12M 29/04; C12M 47/02; G01N 15/06; G01N 15/1404; G01N 15/1459; G01N 15/1484; G01N 1/4077;
(Continued)

(56) References Cited

U.S. PATENT DOCUMENTS

| 5,501,893 A | 3/1996 | Laermer et al. |
| 6,531,068 B2 | 3/2003 | Laermer et al. |
| 2015/0300939 A1* | 10/2015 | Ma .................... G01N 1/4077 435/29 |

OTHER PUBLICATIONS

Abe, S., Steinmann, B. U., Wahl, L. M., & Martin, G. R. (1979). High cell density alters the ratio of type III to I collagen synthesis by fibroblasts. Nature, 279(5712), 442.
(Continued)

*Primary Examiner* — Dean Kwak
(74) *Attorney, Agent, or Firm* — NIXON & VANDERHYE (57) ABSTRACT

A crossflow microfluidic particle concentrator including a main channel having an inlet and an outlet a crossflow outlet operably connectable with pressure means and/or flow control means, a plurality of crossflow channels fluidically connecting the crossflow outlet with the main channel a filtering element including a particle flow channel within the main channel, and a row of crossflow pillars disposed between the filtering element and the plurality of crossflow channels.

9 Claims, 8 Drawing Sheets

(51) Int. Cl.
| | |
|---|---|
| *C12M 1/00* | (2006.01) |
| *C12M 3/00* | (2006.01) |
| *G01N 1/40* | (2006.01) |
| *G01N 15/14* | (2006.01) |
| *G01N 15/1404* | (2024.01) |
| *G01N 15/02* | (2006.01) |
| *G01N 15/06* | (2006.01) |
| *G01N 15/075* | (2024.01) |
| *G01N 15/10* | (2006.01) |

(52) U.S. Cl.
CPC ..... *G01N 15/1404* (2013.01); *G01N 15/1484* (2013.01); *B01L 2200/027* (2013.01); *B01L 2200/0647* (2013.01); *B01L 2200/0652* (2013.01); *B01L 2300/0681* (2013.01); *B01L 2400/049* (2013.01); *G01N 2001/4088* (2013.01); *G01N 2015/0288* (2013.01); *G01N 15/06* (2013.01); *G01N 15/075* (2024.01); *G01N 2015/1006* (2013.01); *G01N 15/1459* (2013.01)

(58) Field of Classification Search
CPC ... G01N 2001/4088; G01N 2015/0288; G01N 2015/0693; G01N 2015/1006
See application file for complete search history.

(56) References Cited

OTHER PUBLICATIONS

Dar, A., Shachar, M., Leor, J., & Cohen, S. (2002). Optimization of cardiac cell seeding and distribution in 3D porous alginate scaffolds. Biotechnology and bioengineering, 80(3), 305-312.

Dvir-Ginzberg, M., Gamlieli-Bonshtein, I., Agbaria, R., & Cohen, S. (2003). Liver tissue engineering within alginate scaffolds: effects of cell-seeding density on hepatocyte viability, morphology, and function. Tissue engineering, 9(4), 757-766.

H. Sekine, T. Shimizu, K. Hobo, S. Sekiya, J. Yang, M. Yamato, H. Kurosawa, E. Kobayashi, and T. Okano, "Endothelial cell coculture within tissue-engineered cardiomyocyte sheets enhances neovascularization and improves cardiac function of ischemic hearts", Circulation, vol. 118, No. 14.

K. Funatsu, H. Ijima, K. Nakazawa, Y. I. Yamashita, M. Shimada, and K. Sugimachi, "Hybrid artificial liver using hepatocyte organoid culture", Artif. Organs, vol. 25, No. 3, pp. 194-200, 2001.

Kim, D. S., Lee, M. W., Ko, Y. J., Chun, Y. H., Kim, H. J., Sung, K. W., . . . & Yoo, K. H. (2016). Cell culture density affects the proliferation activity of human adipose tissue stem cells. Cell biochemistry and function, 34(1), 16-24.

R. L. Mauck, C. C. B. Wang, E. S. Oswald, G. A. Ateshian, and C. T. Hung, "The role of cell seeding density and nutrient supply for articular cartilage tissue engineering with deformational loading", Osteoarthr. Cartil, vol. 11, No. 12, pp. 879-890, 2003.

Radisic, M., Euloth, M., Yang, L., Langer, R., Freed, L. E., & Vunjak-Novakovic, G. (2003). High-density seeding of myocyte cells for cardiac tissue engineering. Biotechnology and bioengineering, 82(4), 403-414.

* cited by examiner

MICRO-FLUIDIC PARTICLE CONCENTRATOR AND FILTERING DEVICE

CROSS-REFERENCE TO RELATED APPLICATIONS

The present patent application is a divisional patent application of the U.S. patent application Ser. No. 16/052,793 that was filed on Aug. 2, 2018, and claims foreign priority to the European patent application with the Application No. EP17184837 filed on Aug. 4, 2017, the entire contents of these two references herewith incorporated by reference.

TECHNICAL FIELD

The present invention lies in the field of microfluidics and microfluidic devices.

BACKGROUND ART

In the field of tissue regeneration, three-dimensional (3D) bio-printing holds fantastic promises: from organoids and multicellular printing for research, to full organ printing for patient transplants. However, even though bio-printers have undergone improvements, the dispensing methods still lack critical functionalities essential to mimic the anatomy of organs.

In literature, the importance of cell seeding density in 3D cultures is often highlighted as a critical parameter in cell behavior modulator [1-4]. It has been shown that seeding at high density, typically between $10^7$ cells per milliliter (ml), improves cell viability [5], growth factor concentration [6] as well as overall cell behavior [7, 8]. However the manipulation of solutions containing high cell densities can be challenging especially in the context of 3D printing. Indeed, most extrusion based printers feature long tubing to bring cells from a container to the printing head. Conveying high cell density solutions through those tubing would lead to massive cell loss in dead volume as well as reduced viability because of cell lysis. For those reasons most printed tissues by extrusion features cell densities revolving around $10^6$ cells per milliliter (ml).

Accordingly, in light of the above described deficiencies of the background art, it would be highly desirable to have devices allowing the concentration of cells on chip just before printing, thus allowing the printing of tissues containing high cell density without the hurdle of manipulating highly concentrated solutions.

SUMMARY

In order to address and overcome the shortcomings of the prior art, the inventor created an optimized microfluidic device that acts as a crossflow particle concentrator and/or purifier, with a particular focus on a novel approach to bring cell concentration functionality to the printing heads of an extrusion-based bio-printer. One of the aspects of the present invention is to provide for a simple and efficient method and device to concentrate particles, particularly cells, in an interface easily adaptable to external devices such as Fluorescence-activated cell sorters (FACS) or 3D bio-printers.

Still another aim of the invention was to optimize the devices known in the art in terms of particle rolling and flow/crossflow balance.

All those aims have been accomplished through the microfluidic device, presented herein, as described hereinafter. In an implemented embodiment, the microfluidic device features a flow channel into which particles to be collected converge from an inlet to an outlet in such a way that a concentration gradient forms along the channel, due to the action of pressure/flow means connected thereon. This is obtained thanks to two parallel rows of pillars of different shapes and distribution acting on the optimization of the particles' flow into the channel and a crossflow providing a tangential filtration. The microfluidic device has been successfully used as an interface between a particles' (cells) source and a bio-printer, allowing a much more efficient production of a cell-loaded biomaterial for tissue engineering.

Accordingly, according to one aspect of the present invention, a crossflow, microfluidic particle concentrator device is provided, preferably comprising:
 a. A main channel having an inlet and an outlet;
 b. A crossflow outlet operably connectable with pressure means or flow control means;
 c. A plurality of crossflow channels fluidically connecting the crossflow outlet with the main channel;
 d. A filtering element defining a particle flow channel within the main channel; and
 e. A row of crossflow pillars disposed between the filtering element and the crossflow channels.

In a preferred embodiment, the filtering element includes or consists of a row of filtering pillars.

In a preferred embodiment, the crossflow channels are evenly distributed along the main channel.

In one embodiment, the filtering pillars and/or the crossflow pillars are evenly distributed along the main channel.

In preferred embodiments, the microfluidic particle concentrator is characterized in that the flow channel runs coaxially compared to the main channel.

In preferred embodiments, the microfluidic particle concentrator is characterized in that the pillars of the row of filtering pillars have a triangular, drop or trapezoidal cross-section.

In preferred embodiments, the microfluidic particle concentrator is characterized in that the pillars of the row of crossflow pillars have a square, round or trapezoidal cross-section.

In some embodiments, the microfluidic particle concentrator is made of a metallic material and/or glass and/or a plastic material and/or silicon. Preferably, the microfluidic particle concentrator is not made of an elastomeric material. Preferably, the row of evenly disposed filtering pillars is not made of an elastomeric material.

According to another aspect of the present invention, a method for manufacturing a crossflow microfluidic particle concentrator is provided, including a step of disposing a row of crossflow pillars between a filtering element, defining a particle flow channel, and a crossflow outlet.

According to yet another aspect of the present invention, a method for providing a particle concentration in a fluid is provided. The method is preferably performed on a fluidic device including a main channel having an inlet and an outlet, a crossflow outlet fluidically connected via a plurality of crossflow channels to the main channel, a filtering element including a particle flow channel within the main channel, and a row of crossflow pillars disposed between the filtering element and the plurality of crossflow channels.

Moreover, the method preferably comprising the steps of introducing the fluid to the inlet of the main channel, the fluid including particles, providing a pressure at the inlet and/or the outlet to cause the fluid to move from the inlet towards the outlet, providing a negative pressure to the crossflow outlet to attract the fluid and the particles towards the crossflow outlet, via the filtering element, the row of crossflow pillars, and the plurality of crossflow channels, and dispensing the fluid with the outlet.

Still another object of the present invention relates to the use of a crossflow, microfluidic particle concentrator according to the invention as a nozzle for a 3D printer.

Still another object of the present invention relates to a nozzle for a 3D printer, characterized in that it comprises a crossflow, microfluidic particle concentrator according to the invention.

Still another object of the present invention relates to a 3D printer having a nozzle according to the crossflow microfluidic particle concentrator device.

Still another object of the present invention relates to the use of a crossflow microfluidic particle concentrator device as a purifier for FACS samples.

Still another object of the present invention relates to purifier for FACS samples, including crossflow microfluidic particle concentrator device.

Still another object of the present invention relates to a FACS apparatus characterized in that it comprises purifier for FACS samples.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the representations in FIGS. 1-8 are simplified for illustration purposes and may not be depicted to scale.

DETAILED DESCRIPTION OF THE SEVERAL EMBODIMENTS

The present disclosure may be more readily understood by reference to the following detailed description presented in connection with the accompanying figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

Figure 1:
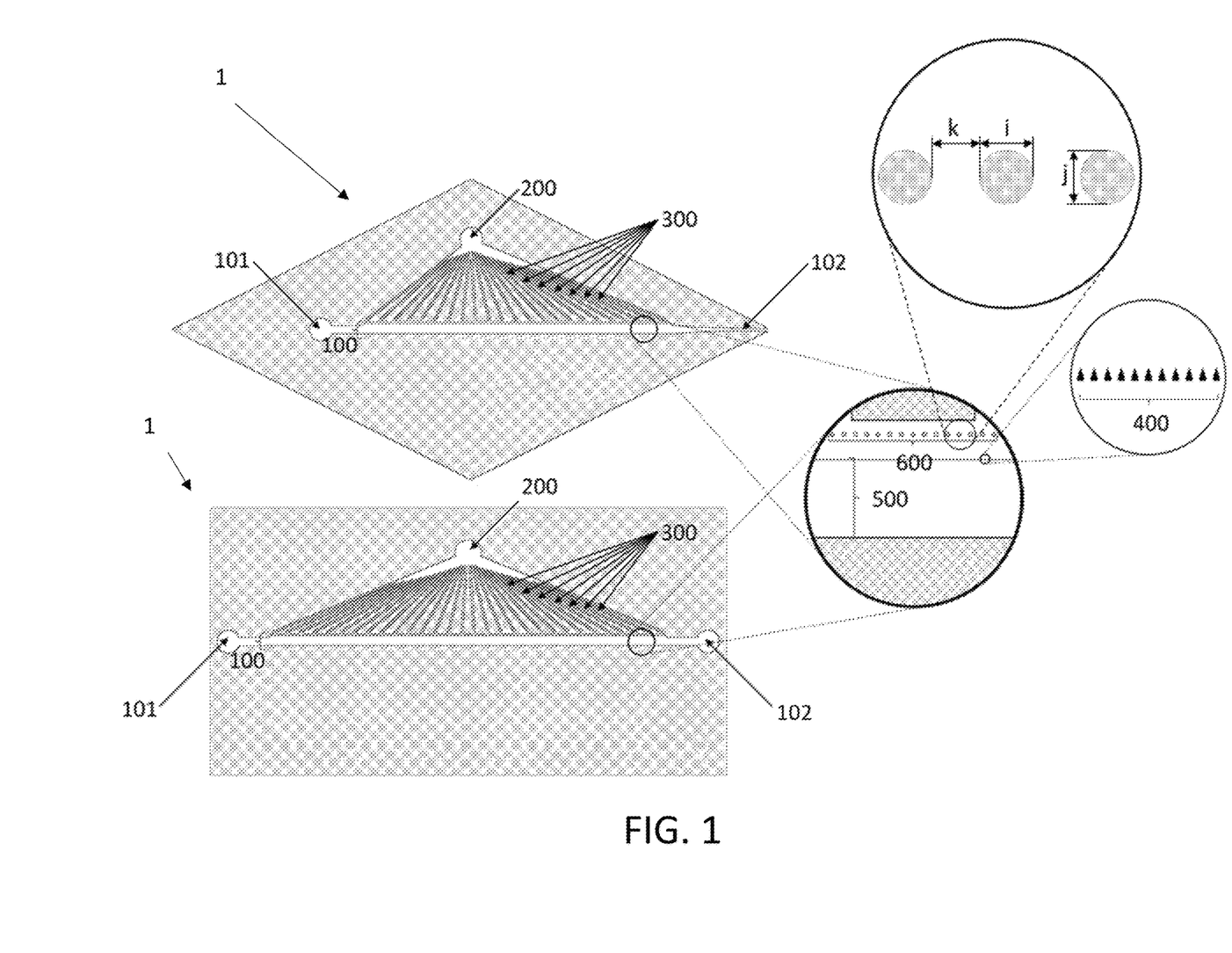
FIG. 1 shows an exemplary view of first embodiment of the crossflow microfluidic particle concentrator according to an aspect of the invention, including three (3) close-up cross-sectional top views.

With reference to FIG. 1, a crossflow microfluidic particle concentrator device 1 (also hereinafter referred to as "the device") according to one embodiment of the invention is shown. The crossflow microfluidic particle concentrator device 1 comprises main channel 100 having an inlet 101 and an outlet 102; a crossflow outlet 200 operably connectable with pressure or flow control means 700' (shown in FIG. 7); a plurality of crossflow channels 300 fluidically connecting the crossflow outlet 200 with the main channel 100; a filtering element 400 composed of a first row of evenly distributed filtering pillars, defining a particle flow channel 500 within the main channel 100; and a second row of evenly distributed crossflow pillars 600 disposed in the main channel 100 between the row of filtering pillars 400 and the crossflow channels 300.

The crossflow microfluidic particle concentrator device 1 includes a series of crossflow channels 300 that connect a main flow channel 100 with a crossflow outlet 200, and two sets of filtering element 400 having first and second rows of pillars for the optimization of the straight and tangential flow of a fluid flowing within the main flow channel 100. The crossflow microfluidic particle concentrator device 1 is intended as a particle concentrator for colloidal solutions such as cell-laden gels or cell-containing media, and can be used in applications such as bio-printing or FACS/flow cytometry for example but not limited to purification, concentration and/or sample enrichment purposes.

A "microfluidic device", "microfluidic chip" or "microfluidic platform" is generally speaking any apparatus which is conceived to work with fluids at a micro/nanometer scale.

Microfluidics is generally the science that deals with the flow of liquids inside channels of micrometer size. At least one dimension of the channel is of the order of a micrometer or tens of micrometers in order to consider it microfluidics. Microfluidics can be considered both as a science (study of the behavior of fluids in micro-channels) and a technology (manufacturing of microfluidics devices for applications such as lab-on-a-chip). These technologies are based on the manipulation of liquid flow through microfabricated channels. Actuation of liquid flow is implemented either by external pressure sources, external mechanical pumps, integrated mechanical micropumps, hydrostatic pressures or by combinations of capillary forces and electrokinetic mechanisms.

The microfluidic technology has found many applications such as in medicine with the laboratories on a chip because they allow the integration of many medical tests on a single chip, in cell biology research because the micro-channels have the same characteristic size as the cells and allow such manipulation of single cells and rapid change of drugs, in protein crystallization because microfluidic devices allow the generation on a single chip of a large number of crystallization conditions (temperature, pH, humidity . . . ) and also many other areas such as drug screening, sugar testers, chemical microreactor or micro fuel cells.

According to some other aspects of the present invention, the crossflow microfluidic particle concentrator device 1 can be easily adapted to work with fluid volumes, particularly liquids, spanning from milliliters (ml) down to femtoliters, and the dimensions can be adapted accordingly to have channels within the millimeter (mm) scale, without substantially departing from the basic principle of operation of the above-described microfluidic device.

For the sake of clarity, as used herein, the wording "operably connected", "operably connectable" or even "operably connecting", reflects a functional relationship between two or more components of a device or a system, that is, such a wording means that the claimed components must be connected in a way to perform a designated function. The "designated function" can change depending on the different components involved in the connection; for instance, the designated function of pressure means operably connected to an outlet is the ability to apply a positive or negative pressure within the outlet in a way as to allow the flowing of its content, or at least a part of it, throughout a channel. A person skilled in the art would easily understand and figure out what are the designated functions of each and every component of the device or the system, as well as their correlations, on the basis of the present disclosure.

For "crossflow particle concentrator" is herein meant a device acting on a liquid or semi-solid medium, such as a (hydro)gel, comprising a plurality of particles by concentrating by crossflow filtration Its particles content along a path on which the medium flows. "Crossflow filtration", also known as "tangential flow filtration", is a type of filtration in which the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, unlike batch-wise dead-end filtration, in which the feed is passed through a membrane or bed, the solids trapped in the filter and the filtrate released at the other end. In crossflow filtration, the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate. In the context of the present invention, the crossflow action of the device is used to wash away the liquid medium (permeate) of a colloidal solution comprising microparticles so that the final solution results more concentrated in microparticles (retentate) when sorting out of the device compared to its entry point.

In operation, the crossflow microfluidic particle concentrator 1 works as follows. A solution comprising a plurality of microparticles is injected or otherwise disposed into the main channel 100 via the main channel inlet 101 through pressure means 700 operably connected thereto (See FIGS. 1 and 7). The pressure means 700 fluidically connect a source of microparticles, such as a reservoir filled with a solution comprising a plurality of microparticles, to the main channel 100 in such a way that the microparticles can flow throughout the main channel 100 upon a suitable pressure change. For instance, a positive or negative pressure can be applied through the main channel 100 via its inlet 101 or its outlet 102, respectively, through pressure means 700. For "positive pressure" is herein meant an applied pressure that increases the main channel 100 internal fluid pressure, whereas for "negative pressure" it is herein meant an applied pressure that diminishes the main channel 100 fluid pressure, as in case of a suction. Means to apply a pressure will usually be coupled with a source of microparticles either directly or indirectly (via e.g. a connection tube).

With respect to the pressure means 700 that can control a flow of the crossflow microfluidic particle concentrator 1, there are three main classes of systems to control liquid motion in microfluidic devices. Some systems use a pressure difference to control the flow rate (hydrostatic or pressure generators), whereas other systems can directly impose a flow rate (syringe pumps). Finally, liquid pumps and electro-osmotic pumps can be used to generate a liquid flow that will depend on the fluidic resistance of the device. Suitable means of altering the pressure or the flow within the device are external or integrated pumps or micropumps, combinations of capillary forces and electrokinetic mechanisms, hydrostatic pressure or simply a syringe. Hydrostatic pressure is the simplest way to generate controlled flows in a microfluidic system. The pressure difference is obtained by varying the altitude of the liquid to atmosphere interface in different reservoirs. For water based liquids, the difference of 1 cm corresponds to 1 mBar, which limits the resolution of this technique to 0.1 mBar and the maximal pressure to 100 mbar (1 m of difference of height). Pressure generators are typically composed of a pressure source (compressor, bottle), a static membrane pressure regulator and a manometer to monitor the pressure value as regard to the atmosphere pressure. The robustness and precision of these systems highly depend on a good compatibility of all the components.

A possibility to quickly change the pressure is the use of several pressure generators with a pressure multiplexor that can be computer-controlled and allows to switch from one pressure to another in a few μs. Another possibility is to control the pressure using a set of electro-valves enslaved electronically to a pressure sensor. The advantage of this technology is the quick response that can be achieved with microvalves. This type of pressure regulator is well fitted for applications requiring sophisticated pressure patterns (gradient or sinusoidal pressure variation for example), precision and fastness but may be fragile compared to static pressure regulators when overpressures or liquids enter the system. Pressure generators can also be associated with flow sensors to ensure a flow-rate control instead of a pressure control (in this case a flowrate feedback control is integrated to the pressure generator). Syringe pumps are the first flow controller used in microfluidics. The main advantage of syringe pumps is their capability to control the flow rate across microchannels independently of the fluidic resistance (the pressure automatically adapts to maintain the flow rate). A syringe pump stabilizer can be used to absorb and dampen the flow rate fluctuations. Liquid pumps such as peristaltic or piezo-electric pumps are still further alternatives. Peristaltic pumps show the main advantage of using interchangeable flexible tubes (limiting the contamination problems) and are fitted for large flow rates applications. Piezoelectric pumps are the most compact pumps and can be used for intermediate flow rates (μL).

Electro-osmotic pumps are based on the electrical pumping of liquid through nano-porous materials. These systems can also withstand larger back pressures but require to work with low conductivity liquids and suffer from a lack of reproducibility. Preferably, means for applying a pressure 700 can be operated and regulated by an external controller, such as a pressure flow controller, a vacuum flow controller, a mechanical flow controller and the like, which can be embedded in a higher robotic system and possibly handled by a computer-like device.

Figure 7:
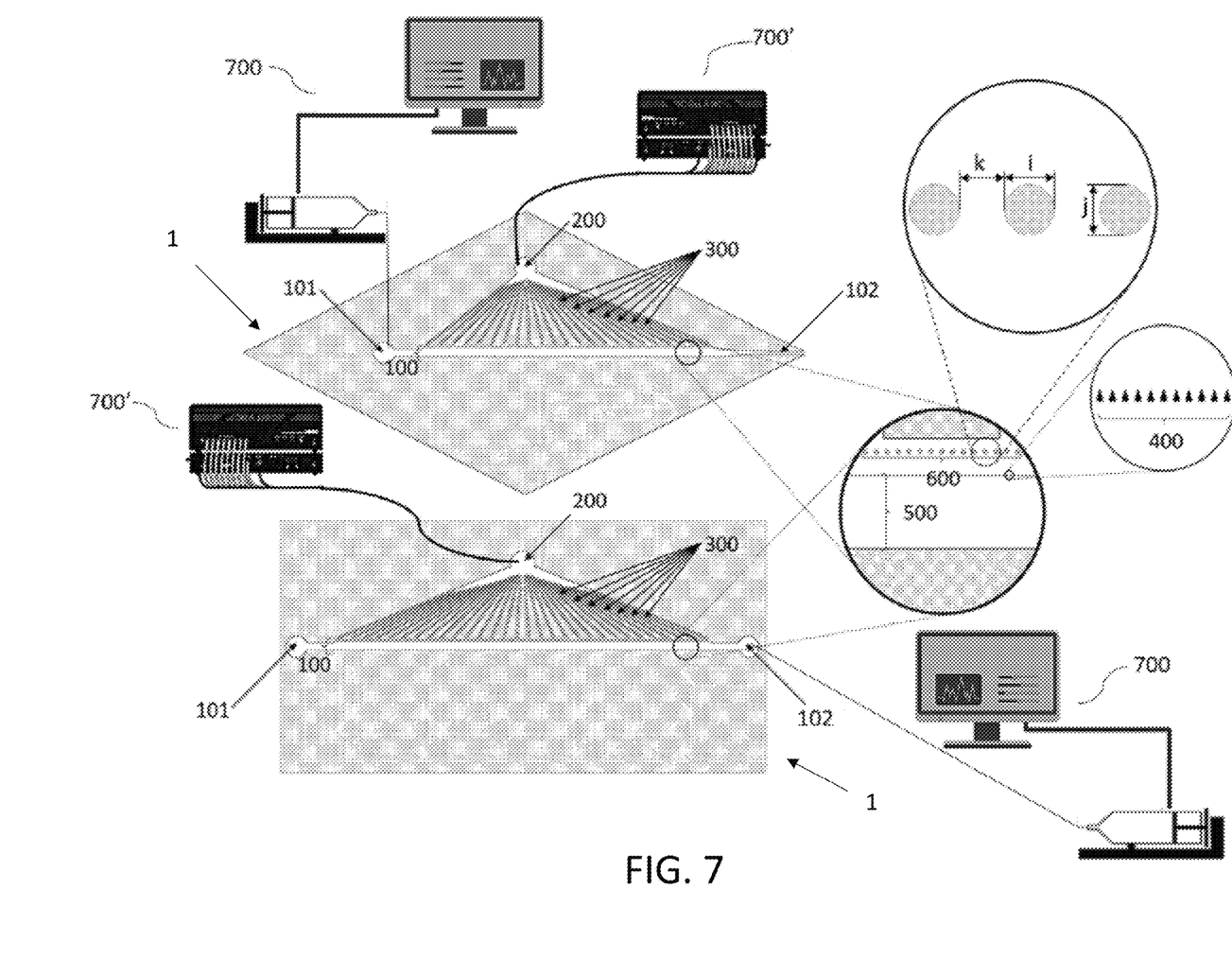
FIG. 7 shows exemplary views of first embodiment of the crossflow microfluidic particle concentrator according to an aspect of the invention operably connected with means for altering the pressure and/or the flow within the device, namely a syringe pump fluidically connected with an inlet, as well as a fluidic pump connected with a crossflow outlet (see upper section of FIG. 7), and a syringe pump fluidically connected with an outlet, as well as a fluidic pump connected with a crossflow outlet (see lower section of FIG. 7)

As exemplarily shown in FIG. 7, the crossflow microfluidic particle concentrator device 1 can be fluidically and operably connected with a computer-handled, syringe-based pumping system 700 configured to impose a positive pressure on inlet 101 of the main channel 100, exemplarily shown in the upper section of FIG. 7, or configured to impose a negative pressure on outlet 102 of the main channel 100, exemplarily shown in the lower section of FIG. 7. Based on the above discussion, some aspects of the invention cover a system that includes a crossflow microfluidic particle concentrator device 1as defined above and pressure/flow means 700 operably connected to its inlet 101 and/or its outlet 102 adapted to generate a pressure within the inlet 101 and/or outlet 102, in a way as to allow the flow of its (their) content, or at least a part of it. Alternatively or additionally, the inlet 101 can comprise, or can be shaped so to include, a reservoir adapted to accommodate a solution comprising a plurality of microparticles.

Within the main channel 100, a first filtering element 400 is disposed so to define a particle flow channel 500 within the main channel 100. The filtering element can be embodied as a stripe, or "wall", having a height such that a liquid is allowed to flow above or below it while impeding the passage of particles such as cells, or can be embodied as a row of filtering pillars, the plurality thereof forming the filtering element 400. Combination of both configurations are even possible.

In some embodiments, the filtering pillars 402 (FIG. 2) are evenly distributed along the main channel 100. For "particle flow channel" is herein meant a channel defined by at least a filtering element such as a first row of filtering pillars 402 that allows and facilitate the flow of microparticles contained within a colloidal solution without letting them escape tangentially. In the embodiment shown in FIG. 1, the particle flow channel 500 runs substantially coaxially compared to the main channel 100, in such a way as to facilitate the design of the entire device, optimize the (linear and tangential) flows and to adopt the less pressure sources as possible.

The filtering element, such as the first row of evenly distributed filtering pillars 402 depicted in FIG. 1, is conceived and implemented to work as a first filter for crossflow filtration. In fact, the filtering pillars 402 have a shape and/or a distribution along the particle flow channel 500 that permit the tangential filtering of the liquid/semisolid medium of a colloidal solution without allowing the passage of microparticles therethrough. The wall or the pillars 402 are disposed or preferably fabricated/patterned on at least one surface of the substrate constituting, for example the floor or the roof of the device, which in the vast majority of the cases is a flat microfluidic chip.

In embodiments envisaging the presence of a wall, the gap through which the liquid is allowed to tangentially flow has a height typically spanning from 0.1 μm to 50 μm. In embodiments envisaging the presence of pillars, these are shaped as regular or irregular polyhedral pillars having a height h, a length a and a depth d, and are separated by void interspaces hereinafter referred to as grooves g, exemplarily shown in FIG. 2. A pitch p defines the interspace between the same points of two adjacent filtering pillars 402.

The filtering element 400 can be an integral portion of the substrate stemming directly from the surface of this latter, or can be integrated on the substrate by e.g. adhesives. In a preferred embodiment, a substrate is shaped to include on a surface thereof the filtering element 400, which is therefore made of the same material. For instance, the substrate can be molded as a unitary, integral body of plastic from any suitable standard polymer material known in the art (e.g., polystyrene, polypropylene, polycarbonates, polysulfones, polyesters, cyclic olefins and so forth) using well-known injection molding methods. Alternatively or additionally, glass, metallic materials, silicon or combinations of the foregoing can be used for the device's manufacturing. Preferably, the microfluidic device is not made of an elastomeric material, particularly for what concerns the filtering element 400, in the example shown a first row of filtering pillars 402.

Preferably, the plurality of filtering pillars 402 have an aspect ratio, i.e. the ratio h/a and/or h/d between the height and the lateral feature size of each filtering pillar 402, comprised between 1 and 50, such as for instance 2.5, 1.5, 1.25, 2.75, 10.5 or 20.3. Furthermore, a ratio a/d spanning from 0.5 to 5 is preferred to diminish fluidic resistance between pillars, avoiding particles to pass through.

In some embodiments, the length a and the depth d of the filtering pillars 402 are equal, which is typically the case of some parallelepiped, cubic, polygonal or cylindrical pillars, and can be measured at the basis or at the top of the pillars. Furthermore, in some embodiments, the ratio between the lateral sizes a and/or d of each filtering pillar 402 and the groove g (i.e., the a/g and/or d/g ratio) is preferably comprised between 0.5 to 10 for both ratios.

The dimensions h, a, d and g of the pillars 402 can usually span from 0.1 to 200 μm, such as for instance h being in a range from 10 μm to 200 μm; a and/or d: from 1 μm to 25 μm; g: from 0.1 μm to 10 μm; p: from 2 μm to 15 μm.

In preferred embodiments, filtering pillars 402 are shaped as elongated parallelepipeds having a triangular cross-section, wherein one side of the triangle is directed towards the lumen of the particle flow channel 500. This embodiment minimizes the fluidic resistance between the pillars, preventing particles to get stuck and allow them to roll against the pillars while flowing along the particle flow channel 500.

In order to concentrate microparticles within a medium or fluid in which they are suspended in, a crossflow is applied to the device. The crossflow is applied substantially perpendicular to the flow of the medium experienced within the main channel 100, and it is provided by applying e.g. a negative pressure (i.e. a suction) from a crossflow outlet 200 operably connected with pressure/flow means 700'. The suction acts on a plurality of crossflow channels 300 fluidically connecting the crossflow outlet 200 with the main channel 100. The ratio between the flow in the channel 100 and the crossflow in channels 300 can span form 0 to 0.99 to produce any desired concentration. Preferably, means for applying a pressure 700' can be operated and regulated by an external controller, such as a pressure flow controller, a vacuum flow controller, a mechanical flow controller and the like, which can be embedded in a higher robotic system and possibly handled by a computer-like device.

Figure 2:
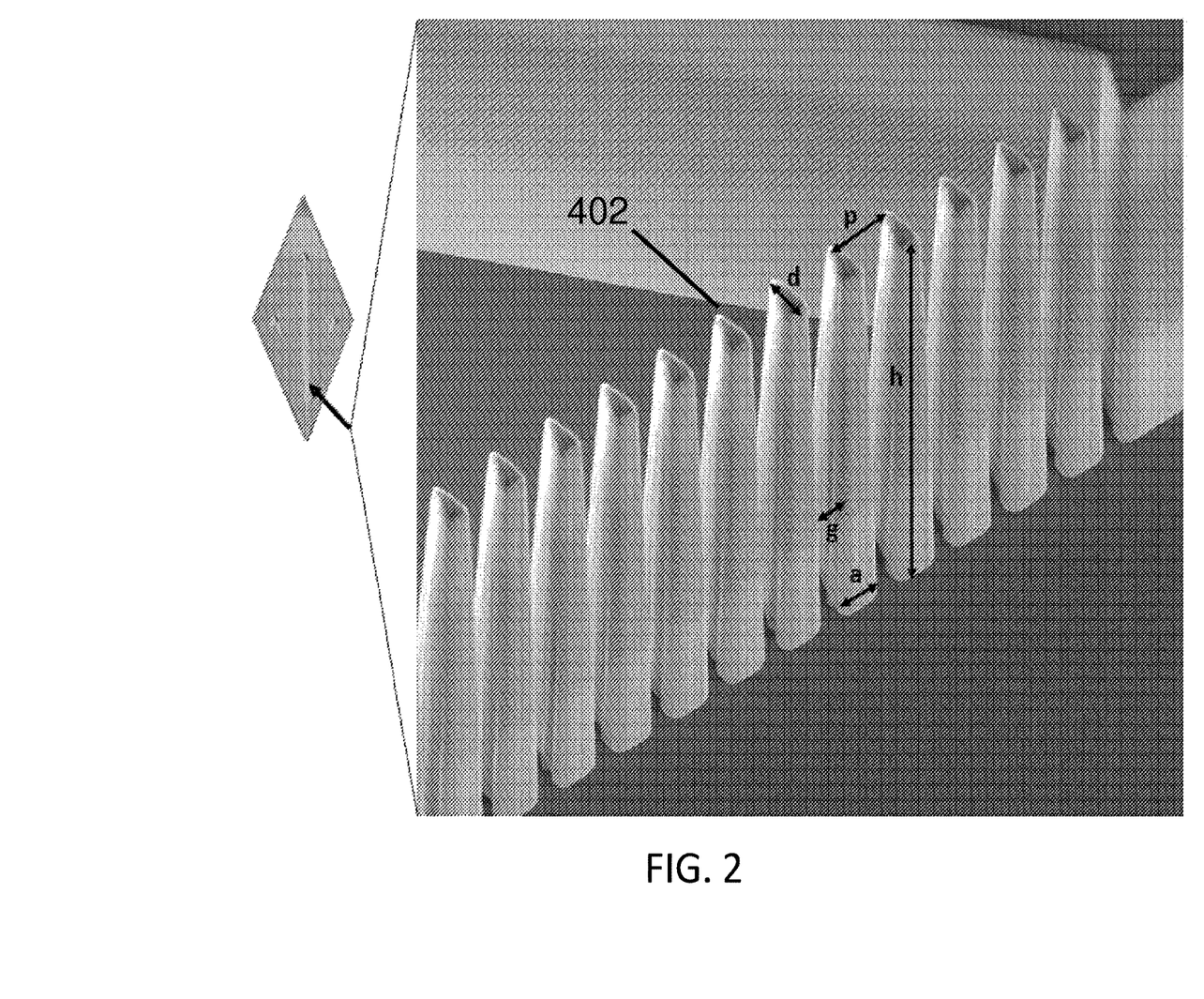
FIG. 2 shows a perspective exemplary representation of one embodiment with a row of filtering pillars having a triangular cross-section according to an aspect of the invention.
Figure 3:
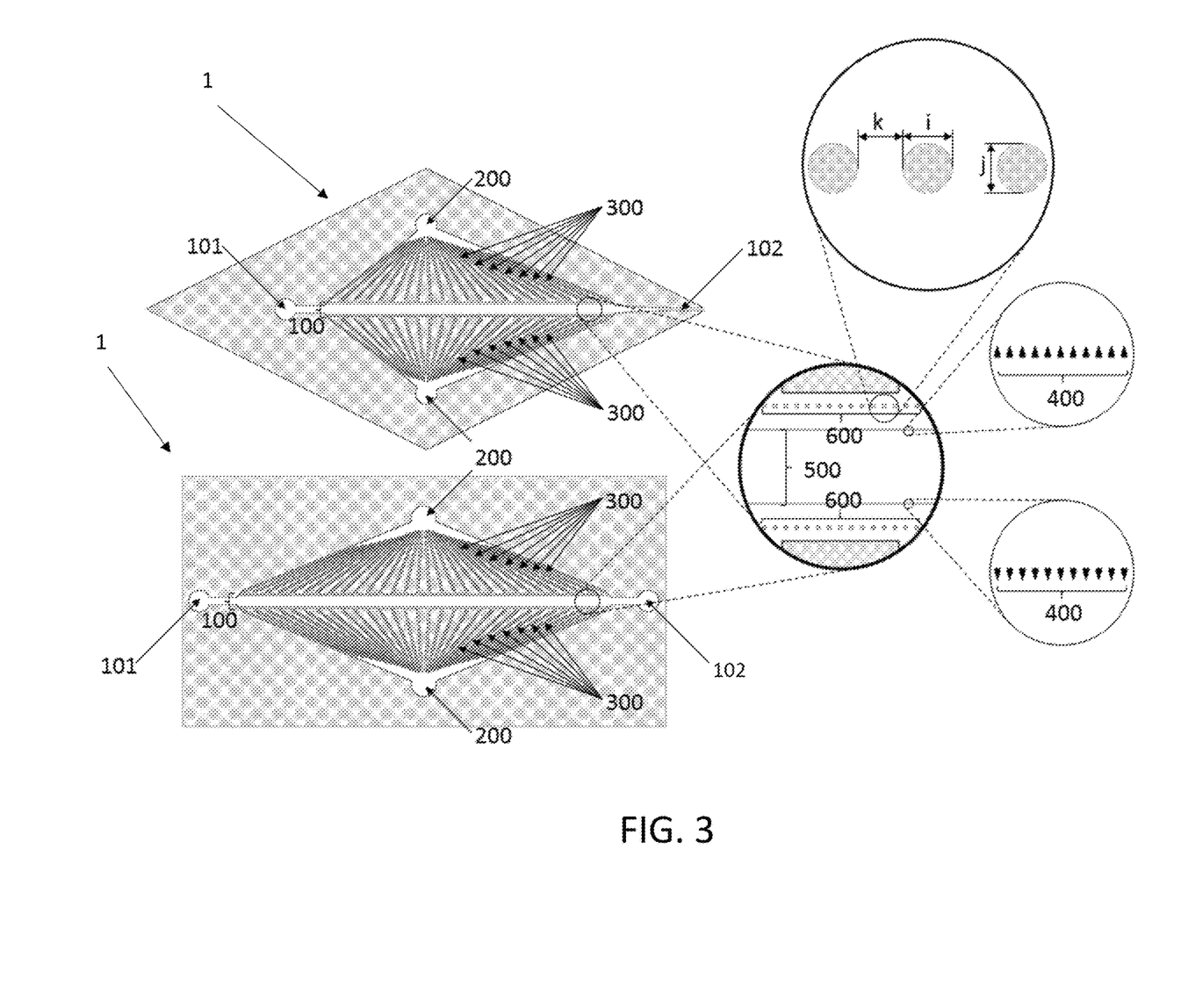
FIG. 3 shows an exemplary view of a second embodiment of the crossflow microfluidic particle concentrator according to another aspect of the invention, having two crossflow outlets to reduce operation times.
Figure 4A:
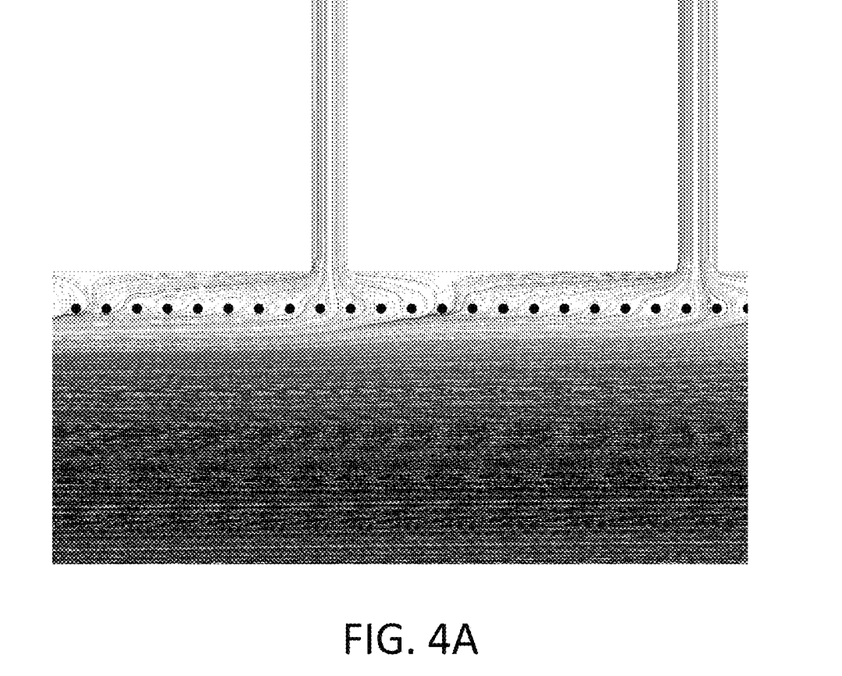
FIGS. 4A and 4B show a cross-sectional view of a simulation of the tangential flow for two different embodiments of evenly spaced crossflow pillars having a round (FIG. 4A) or square (FIG. 4B) cross-section.
Figure 4B:
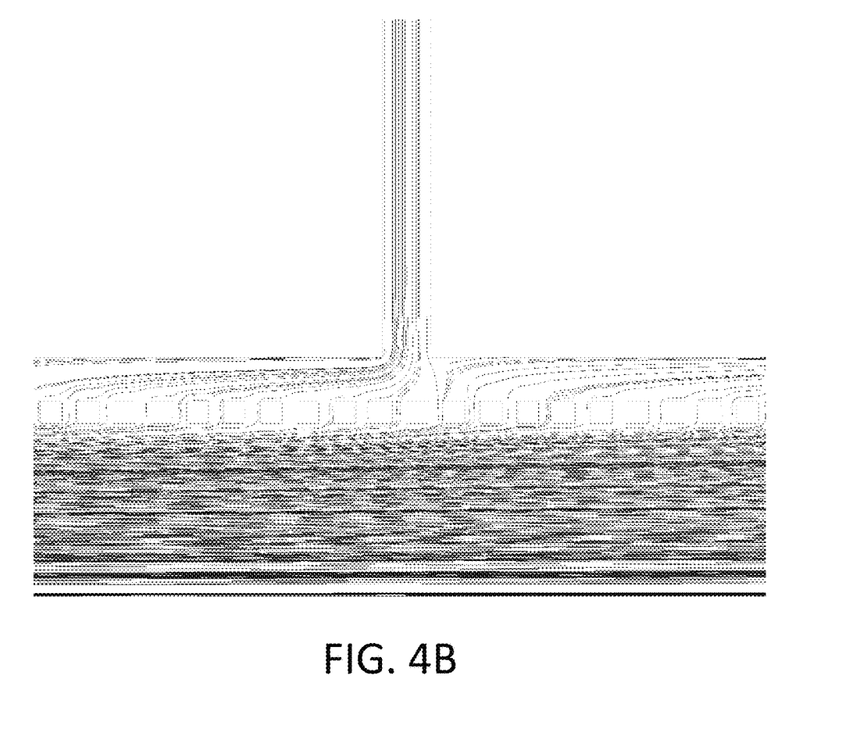

In order to optimize the crossflow homogeneity, a second row of e.g. evenly distributed crossflow pillars 600 are disposed between the flow channel 500 and the main channel 100, i.e. they are positioned between the filtering element 400 and the crossflow channels 300, see FIGS. 4A and 4B. Typically, the second row of crossflow pillars 600 runs in parallel to the filtering element 400. The crossflow pillars 600 have a height h, a length i and a depth j, and are separated by void interspaces hereinafter referred to as grooves k. The pitch p of the filtering pillars 402 is smaller than the interspaces (pitch) k of the crossflow pillars 600. A distance (grooves) g between two neighboring filtering pillars 402 is smaller than a distance (grooves) k between two neighboring crossflow pillars 600, as illustrated in FIGS. 2 and 3.

In preferred embodiments, crossflow pillars 600 are shaped in order to maximize the fluidic resistance; for instance, filtering pillars 600 can have a cross-section such as, but not limited to, a square, round or trapezoidal cross-section. The dimensions i, j and k of the pillars 600 can usually span from 5 μm to 100 μm. The accurate choice of the above-referenced features concerning the crossflow pillars 600 permits to optimize the flows inside the microfluidic device, as shown in FIGS. 4A and 4B, in which it can clearly be seen the "slicing" effect of the crossflow pillars 600 on the tangential flow.

In preferred embodiments, the number of crossflow channels 300 are can vary from 1 to 500 in accordance to the maximum flow needed for the application. Their spacing can vary from 0.5 mm to 5 mm.

In one implemented embodiment, the microfluidic device comprises:
a. A main channel 100 having an inlet 101 and an outlet 102;
b. A first and a second crossflow outlet 200 operably connectable with pressure and/or flow control means 700', the first and a second crossflow outlet 200 disposed on opposite sides relative to the main channel 100;
c. A first and a second set of crossflow channels 300 fluidically connecting, respectively, the first and the second crossflow outlet 200 with the main channel 100;
d. Two parallel filtering elements 400, such as rows of evenly distributed filtering pillars, defining a particle flow channel 500 within the main channel 100; and
e. A first and a second row of evenly distributed crossflow pillars 600 disposed between the filtering elements 400 and, respectively, the first and second set of crossflow channels 300, see FIG. 3.

Figure 8:
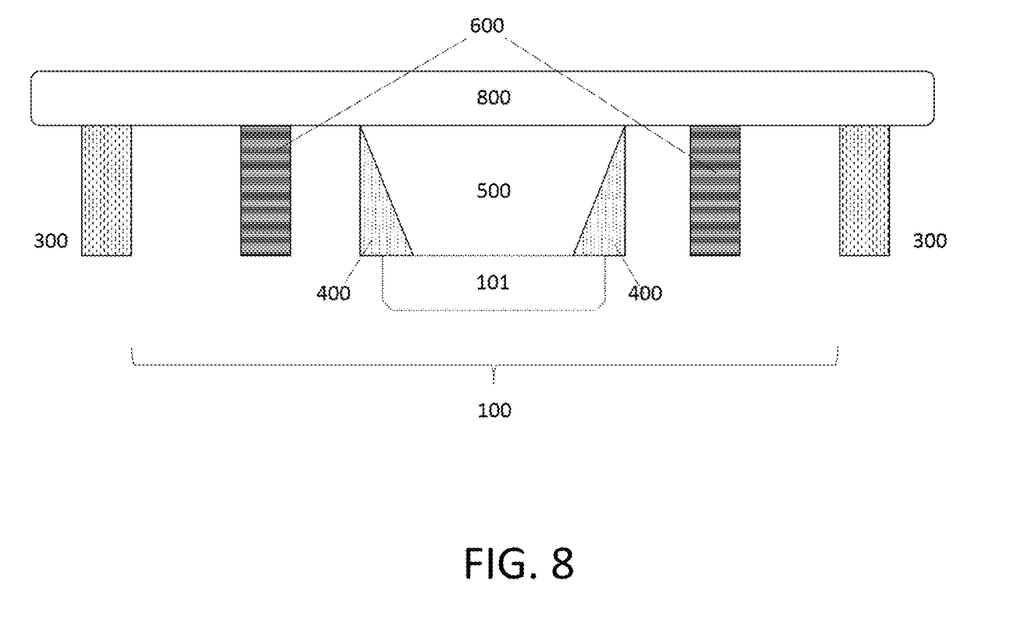
FIG. 8 shows a transverse cross-sectional view of an embodiment of the crossflow microfluidic particle concentrator according to an aspect of the invention, having an encapsulation top layer forming the "roof" of the device.

In another embodiment of the invention, as shown in FIG. 8, the crossflow microfluidic particle concentrator device 1 comprises an encapsulating layer 800 to define the roof of the microfluidic chip. The material composing the encapsulation layer 800 can comprise or consist of materials such as but not limited to glass or polymeric materials such as plastics (e.g., polystyrene, polypropylene, polycarbonates, polysulfones, polyesters, cyclic olefins and so forth). Alternatively, soft polymeric materials such as elastomers, rubber, polyurethane (PU), polyvinylidene fluoride (PVDF) or combinations thereof, can be disposed by e.g. lamination, gluing or anodic bonding, and possibly cured, or by other types of adherence techniques, whenever needed.

The microfluidic device can be used as a concentrator of any kind of microparticles, nanoparticles, and cells, such as such as micro/nanodroplets or micro/nanocapsules, metallic or polymeric micro/nanobeads, or cells, to cite a few. As it will be evident for a person skilled in the art, sizes, shapes and materials of the various components of the microfluidic device could be adapted depending on the needs and circumstances so to fit to the diverse experimental conditions, such as sizes, shapes and materials of the to-be-concentrated particles, the flow rates adopted and so forth.

As used herein, the term "microparticles" relates to particles between 0.1 μm and 1000 μm in size. In the frame of the present disclosure, the term is used indifferently to intend several kind of particles such as droplets, capsules, beads, vesicles, grains and the like. A "microcapsule" is a micrometer-scale particle such as for instance gas bubbles or liquid drops surrounded by a solid, liquid, or otherwise fluid shell. They are also referred to herein as "core-shell capsules". "Vesicles" are one type of capsules that can be designed to storage active ingredients. Their membrane is generally composed of a bilayer of self-assembled amphiphiles. A "double emulsion capsule" is a particle composed of a drop (the core) contained in a second, larger drop (the shell membrane) made of an immiscible, or partially miscible fluid.

Another object of the present invention relates to a method for manufacturing a crossflow microfluidic particle concentrator, the manufacturing method comprising a step of disposing a row of crossflow pillars between a first row of filtering pillars, defining a particle flow channel, and a crossflow outlet. Suitable ways of manufacturing the microfluidic device include etching, lithography, laser machining, 3D printing, hot embossing and so forth. According to an embodiment, the Bosch process, also known as pulsed or time-multiplexed etching described e.g. in U.S. Pat. No. 6,531,068 or 5,501,893, has been used, these U.S. patents herewith incorporated by reference in their entirety.

Still another object of the present invention relates to the use of a crossflow, microfluidic particle concentrator according to the invention as a nozzle for a 3D printer, as well as a nozzle for a 3D printer, characterized in that it comprises a crossflow, microfluidic particle concentrator, and a 3D printer comprising a nozzle.

3D printing is emerging as a complex manufacturing technique, which is suitable in some cutting-edge scenarios for printing biological materials such as bioscaffolds or even biological tissues or organs for tissue engineering/transplantation. This technique offers great precision to control the internal architecture of e.g. a biological scaffold and print complicated structures close in architecture to native tissue. Based on computer-aided design (CAD) models, 3D printers (in such a case, also named "bio-printers") can fabricate a predesigned patient-specific tissue construct in a layer-by-layer fashion. Furthermore, non-invasive imaging techniques of patients' tissues or defects can be obtained and used to inform CAD design, which would allow the scaffold to be a specifically sized implant perfectly fitting into the defect site.

3D printing and rapid prototyping processes have been used to create scaffolds that are 3D with user defined micro-structures and micro-scaled architectures, allowing full control over e.g. the distribution and size of pores and wall material in nearly arbitrary geometries. This ensures that a great many more complex, predesigned architectures patterns and structures can be implemented. Both for hard and soft tissues, interconnected pores, specific pore structures at the micro-scale, and interconnections are very important for the scaffold design. A complicated, hierarchical structure is one that is difficult to replicate, and is more difficult to control with other common scaffold fabrication techniques. With the application of 3D printing, there is an allowance not only for the creation of delicate and intricate structures from the advanced working of strong and robust materials, but the potential to create highly ordered structures that could conceivably match any desired architecture. The three most commonly used 3D printer technologies in medical applications are selective laser sintering (SLS), thermal inkjet (TIJ) printing, and fused deposition modelling (FDM). The main feature of these systems is their ability to print cell-laden gels to yield viable and functional scaffolds. The printers utilize a pneumatic pressurized system to extrude the material from "bioink" cartridges, comprising the biological material of choice.

In the developed 3D printer nozzle, the crossflow microfluidic particle concentrator device is used, for example as embodied by the representation of FIG. 3, operably connected to a reservoir including a medium having a plurality of microparticles (in a specific case, cells) suspended therein through its inlet 101 of the main channel 100. In an implemented embodiment, the printer is a bio-printer, i.e. a 3D printer adapted to manufacture biomaterial s, usually cell-laden biocompatible hydrogels, particularly intended for, but not limited to, e.g. tissue engineering, organoid printing for drug testing. In operation, the cell-laden medium is injected into inlet 101 via injection means 700 integrated into the bio-printer, and at the same time a crossflow is applied by a suction exerted by micropumps 700' on the two crossflow outlets 200. The biomaterial become more concentrated when flowing from the inlet 101 to outlet 102 as a result of the tangential filtration applied.

In some embodiments, as exemplary shown for instance in the upper section of FIG. 7, the outlet 102 is designed to provide for the dispensing of a medium that includes the particles, for example but not limited to a cell-laden biomaterial. Depending on the needs and circumstances, for instance the applications envisaged for the microfluidic device 1, means 700 can apply a positive pressure, also referred to hereinafter as "dispensing pressure", within main channel 100, that imposes the fluid, preferably a liquid or a semi-solid medium including the particles, inside the device to flow out the outlet 102 and makes the particles leave or exit the device. The outlet 102 can be shaped in order to facilitate the dispensing phase, based for instance on the number and/or type of particles to be dispensed, the applied pressure into the inlet 101 by means 700, or the desired outflow, just to cite a few. For instance, the outlet 102 can have a squared or round section with a side/diameter comprised between 1 and 200 μm, such as between 1 and 150 μm, between 1 and 100 μm, between 1 and 50 μm or between 1 and 20 μm, which are suitable values for e.g. dispensing a cell concentrated medium with a continuous flow comprised between 1 and 10 μl/s.

The crossflow microfluidic particle concentrator device can be used in many application including but not limited to, concentration of cells just before printing to achieve relevant cell concentration in printed tissue, concentration of cells in droplet for reliable organoids printing for pharmaceutical applications, concentration of particles to above percolation threshold for electronic printing, concentration of small amount of cells coming from biopsy, filtration by size of particles leaving the large particles pass through opposed to standard filtration methods, filtration of sample coming from enzymatic digestion as purification before performing flow cytometry technics such as fluorescent assisted cell sorting (FACS) to cite a few.

Still another object of the present invention relates to the use of a crossflow microfluidic particle concentrator as a purifier for FACS/flow cytometer samples, as well as a FACS/flow cytometer apparatus by using one or more crossflow, microfluidic particle concentrator. Advantageously, the crossflow microfluidic particle concentrator device can be operably coupled with fluidic lines of a FACS apparatus so to concentrate and purify the sample to be analyzed, and with the further advantage of having an in-line purifier/concentrator so to reduce time and manipulations of the sample. The crossflow microfluidic particle concentrator device is integrated within a FACS apparatus along the fluidic lines, and before the sample flow arrives to the cell injector nozzle in the FACS injector tip, where the sample meets a sheath fluid determining the flow alignment.

Figure 5:
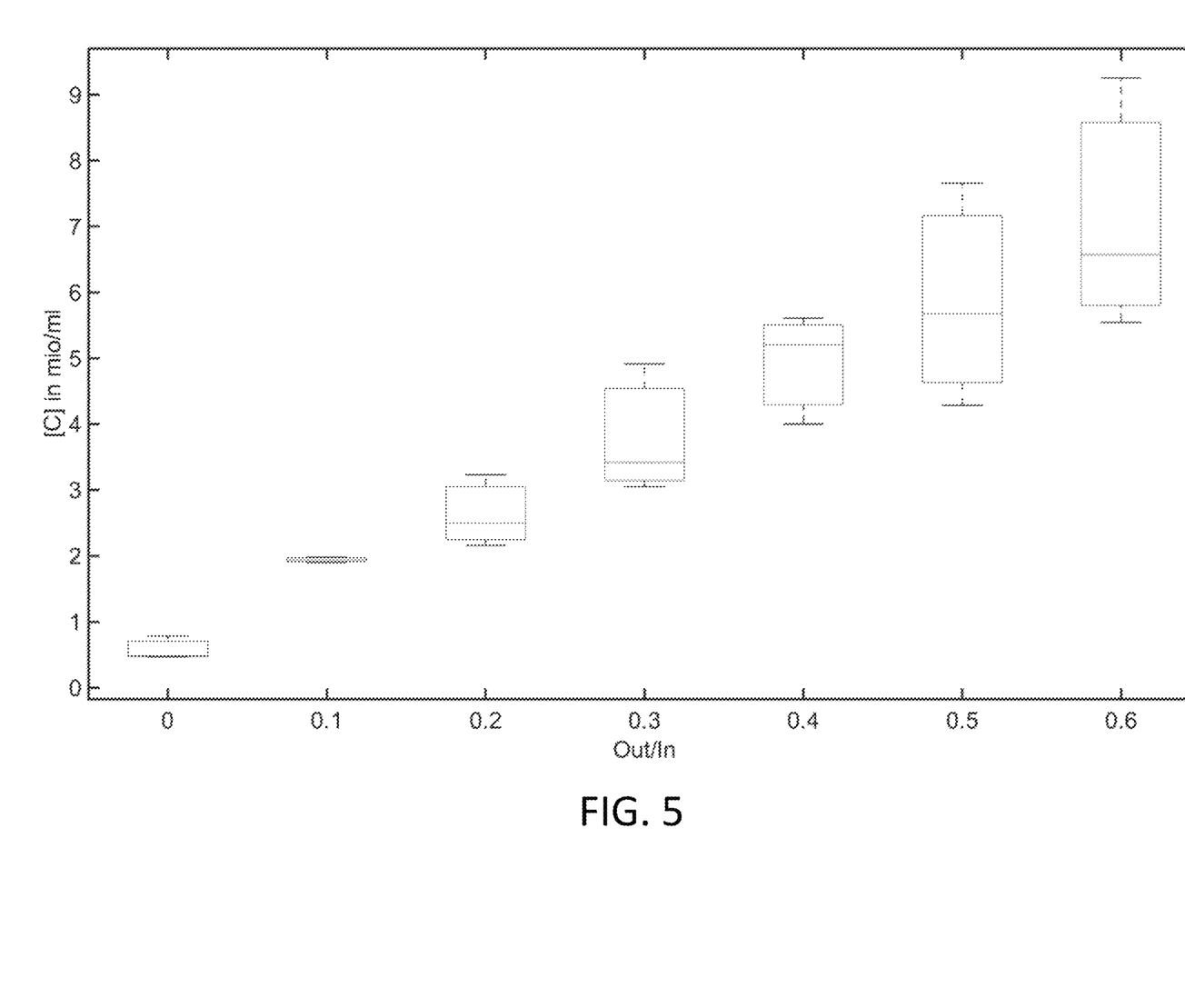
FIG. 5 shows a graph of the concentration of a cell-laden gel solution in comparison with the withdrawal factor.

In one exemplary, non-limiting implemented embodiment, using the Bosch process, microfluidic channels where etched in silicon and sealed with a glass wafer by anodic bonding. The probes where then released by dicing and mounted on a 3D printer to serve as extrusion head for a biomaterial. Each probe features a crossflow filter with the above described dimension allowing cell concentration. A mixture of Alginate 1%, collagen type I 1.5 mg/ml and a cell medium (DMEM with 10% FBS and 1% Penstrep) was prepared, in which 1 million per ml NOR-10 cells were suspended. This solution was printed on a 4% Agarose, 2% CaCl2 bed. By choosing the inlet and outlet speeds with 1 μl/s as inflow in channel 100 and flows spanning from 0.1 μl/s to 0.4 μl/s in channels 300, gels with concentrations spanning from 1 to 10 million cells per milliliter were printed providing a 10 fold concentration with respect to injected solution from inlet 101, see FIG. 5. To assess the cells viability, the gels where put into culture (37° C. and 8% CO2) for three (3) days following printing.

Figure 6:
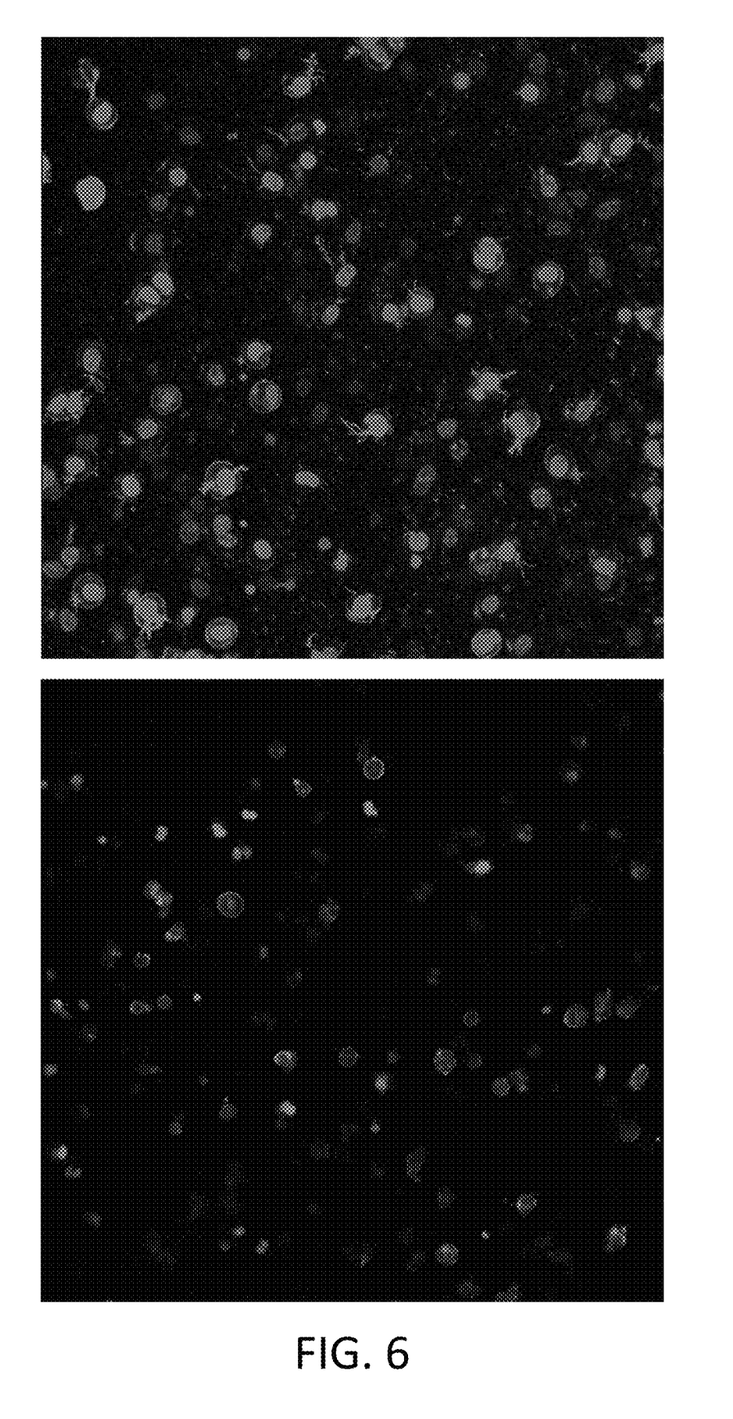
FIG. 6 shows a microscope photography of low (left) vs highly (right) concentrated bio-printed cell-laden gel solutions after three (3) days in culture.

With the crossflow microfluidic particle concentrator device 1, it was possible to print solutions with high cell concentrations while keeping a high cell viability and without losing extensive numbers of cells in tubing. The hydrogels with high cellular concentration were exhibiting noticeable differences with regards to gels at low cellular concentration after only a few days in culture. Cells more densely packed start making dendrites, see FIG. 6, as it is the case in biological tissues, thus without the use of platelet-derived growth factor. This result highlights the importance of relevant cell concentration in bio-printing. The concept can be applied to multiple cell types at the same time to provide more relevant cell densities and organization with what we encounter in biological tissue opening the door to functional tissue printing.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

[1] D. S. Kim, M. W. Lee, Y. J. Ko, Y. H. Chun, H. J. Kim, K. W. Sung, H. H. Koo, and K. H. Yoo, "Cell culture density affects the proliferation activity of human adipose tissue stem cells", Cell Biochem. Funct, vol. 34, No. 1, pp. 16-24, 2016.

[2] K. Funatsu, H. Ijima, K. Nakazawa, Y. I. Yamashita, M. Shimada, and K. Sugimachi, "Hybrid artificial liver using hepatocyte organoid culture", Artif. Organs, vol. 25, No. 3, pp. 194-200, 2001.

[3] M. Dvir-Ginzberg, I. Gamlieli-Bonshtein, R. Agbaria, and S. Cohen, "Liver tissue engineering within alginate scaffolds: effects of cell-seeding density on hepatocyte viability, morphology, and function", Tissue Eng., vol. 9, No. 4, pp. 757-766, 2003.

[4] A. Dar, M. Shachar, J. Leor, and S. Cohen, "Optimization of cardiac cell seeding and distribution in 3D porous alginate scaffolds", Biotechnol. Bioeng, vol. 80, No. 3, pp. 305-312, 2002.

[5] M. Radisic, M. Euloth, L. Yang, R. Langer, L. E. Freed, and G. Vunjak-Novakovic, "High-density seeding of myocyte cells for cardiac tissue engineering", Biotechnol. Bioeng, vol. 82, No. 4, pp. 403-414, 2003.

[6] H. Sekine, T. Shimizu, K. Hobo, S. Sekiya, J. Yang, M. Yamato, H. Kurosawa, E. Kobayashi, and T. Okano, "Endothelial cell coculture within tissue-engineered cardiomyocyte sheets enhances neovascularization and improves cardiac function of ischemic hearts", Circulation, vol. 118, No. 14 Suppl, pp. 145-153, 2008.

[7] G. R. M. Shigeto Abr, Beat U. Steinmann, Larry M. Wahl, "High cell density alters the ration of type III to I collagen synthesis by fibroblasts", Nature, pp. 442-444, 1979.

[8] R. L. Mauck, C. C. B. Wang, E. S. Oswald, G. A. Ateshian, and C. T. Hung, "The role of cell seeding density and nutrient supply for articular cartilage tissue engineering with deformational loading", Osteoarthr. Cartil, vol. 11, No. 12, pp. 879-890, 2003.

The invention claimed is:

1. A system for providing a particle concentration in a fluid, the system comprising:
   a crossflow microfluidic particle concentrator device including
      a main channel having an inlet and an outlet, the main channel defining a main flow direction from the inlet to the outlet,
      a crossflow outlet configured to be fluidically connected to a fluidic device,
      a plurality of crossflow channels fluidically connecting the crossflow outlet with the main channel,
      a filtering element disposed in the main channel and comprising a row of filtering pillars evenly distributed along the main channel, the filtering element defining a particle flow channel along the main flow direction within the main channel,
      a row of crossflow pillars disposed in the main channel between the filtering element and the plurality of crossflow channels, the crossflow pillars being evenly distributed along the main channel, and
      an interspace between the same points of two adjacent ones of the filtering pillars being smaller than an interspace between the same points of two adjacent ones of the crossflow pillars, the interspace between the same points of the two adjacent ones of the filtering pillars being comprised between 5 micrometers and 100 micrometers;
   a device configured to provide a negative pressure to the crossflow outlet to attract the fluid and the particles from the main channel towards the crossflow outlet, through the filtering element and then through the row of crossflow pillars, into the plurality of crossflow channels after passing through the filtering element and the row of crossflow pillars and into the crossflow outlet; and
   a pressure system configured to inject a continuous fluid flow along the main channel in a direction of the main flow direction.

2. The system according to claim 1, wherein a pitch of the crossflow pillars is smaller than a pitch of inlets of the plurality of crossflow channels along the main channel of the crossflow microfluidic particle concentrator device.

3. The system according to claim 1, wherein the filtering element includes a continuous wall element.

4. The system according to claim 1, wherein a distance between two neighboring ones of the crossflow pillars is smaller than a diameter of the plurality of the crossflow channels.

5. The system according to claim 1, wherein each of the filtering pillars has a ratio between a height of the filtering pillar and a length of the filtering pillar comprised between 1 and 50.

6. The system according to claim 1, wherein each of the filtering pillars has a ratio between a height of the filtering pillar and a depth of the filtering pillar comprised between 1 and 50.

7. The system according to claim 1, wherein each of the filtering pillars has a ratio between a length of the filtering pillar and a depth of the filtering pillar comprised between 0.5 to 5.

8. The system according to claim 1, wherein each of the filtering pillars has a ratio between a length of the filtering pillar or a depth of the filtering pillar and the interspace between the same points of two adjacent ones of the filtering pillars comprised between 0.5 to 10.

9. The system according to claim 1, wherein each of the filtering pillars has a triangular cross-section in which one side of the triangle is directed towards the main channel.

* * * * *